United States Patent
Hale et al.

(10) Patent No.: US 7,409,880 B2
(45) Date of Patent: Aug. 12, 2008

(54) SYSTEM USEFUL FOR HOLDING A SAMPLE AND IN SUBJECTING THE SAMPLE TO CHROMATOGRAPHIC ANALYSIS

(75) Inventors: John E. Hale, Fishers, IN (US); Michael D. Knierman, Indianapolis, IN (US); Kirk S. Boraas, Chaska, MN (US)

(73) Assignee: Indiana Proteomics Consortium, LLC, Indianapolis, IN (US)

( * ) Notice: Subject to any disclaimer, the term of this patent is extended or adjusted under 35 U.S.C. 154(b) by 45 days.

(21) Appl. No.: 11/388,722

(22) Filed: Mar. 24, 2006

(65) Prior Publication Data

US 2006/0213258 A1 Sep. 28, 2006

Related U.S. Application Data

(60) Provisional application No. 60/665,783, filed on Mar. 28, 2005.

(51) Int. Cl.
*B01L 3/02* (2006.01)
*G01N 37/00* (2006.01)

(52) U.S. Cl. .................................. 73/864.01; 73/864.91

(58) Field of Classification Search .................. 73/863, 73/863.01, 864.01, 864.21, 864.91, 866.5, 73/861.81–861.87
See application file for complete search history.

(56) References Cited

U.S. PATENT DOCUMENTS

| | | | | |
|---|---|---|---|---|
| 4,748,859 A * | 6/1988 | Magnussen et al. | ...... | 73/864.01 |
| 5,200,151 A * | 4/1993 | Long | ............ | 422/100 |
| 5,209,128 A * | 5/1993 | Whelan | ............ | 73/864.03 |
| 5,496,523 A * | 3/1996 | Gazit et al. | ............ | 422/100 |
| 5,525,302 A * | 6/1996 | Astle | ............ | 422/100 |
| 5,827,745 A * | 10/1998 | Astle | ............ | 436/54 |
| 5,866,072 A * | 2/1999 | Bowe et al. | ............ | 422/78 |
| 6,168,761 B1 * | 1/2001 | Kelly et al. | ............ | 422/100 |
| 6,171,553 B1 * | 1/2001 | Petrek | ............ | 422/100 |
| 6,197,259 B1 * | 3/2001 | Kelly et al. | ............ | 422/100 |
| 6,770,246 B1 * | 8/2004 | Husek | ............ | 422/101 |
| 6,780,381 B2 * | 8/2004 | Yiu | ............ | 422/100 |
| 6,793,891 B2 * | 9/2004 | Yiu | ............ | 422/100 |
| 6,969,850 B2 * | 11/2005 | Staats | ............ | 250/288 |

FOREIGN PATENT DOCUMENTS

| | | |
|---|---|---|
| EP | 0423517 A1 | 4/1991 |
| WO | WO 93/08913 | 5/1993 |
| WO | WO 02/40131 A1 | 5/2002 |
| WO | WO 03/036304 A1 | 5/2003 |

\* cited by examiner

*Primary Examiner*—Hezron E. Williams
*Assistant Examiner*—John Fitzgerald
(74) *Attorney, Agent, or Firm*—Brinks Hofer Gilson & Lione

(57) ABSTRACT

A robotic system for handling components during chromatographic analysis of a sample includes a holder for positioning a sample within a separation pathway, the holder including a first opening having an internally tapered shape and a second opening having an externally tapered shape. An interior of the holder, between the first and second openings, defines the separation pathway. A hollow rigid member has an externally tapered shape, and a receiving portion has an internally tapered shape. The holder is positioned between the hollow rigid member and the receiving portion, wherein the externally tapered hollow rigid member engages the internally tapered first opening and the internally tapered receiving portion receives the externally tapered second opening to provide a sealed separation pathway extending from the hollow rigid member to the receiving portion.

20 Claims, 4 Drawing Sheets

US 7,409,880 B2

SYSTEM USEFUL FOR HOLDING A SAMPLE AND IN SUBJECTING THE SAMPLE TO CHROMATOGRAPHIC ANALYSIS

PRIORITY CLAIM

This application claims priority to Provisional Patent Application No. 60/665,783, filed on Mar. 28, 2005.

BACKGROUND

1. Field of the Invention

The invention generally relates to the field of chromatographic analysis of samples and, more specifically, to the automatic handling of the sample during such analysis.

2. Background of the Invention

In general, the chromatographic analysis of samples containing components of varying molecular weight is not new. Such analysis separates the components of a sample into fractions of increasing or decreasing molecular weight by moving the sample, usually together with a solvent, through a device that is adapted to cause components of differing molecular weight to move at differing speeds. In a typical such device the capillary pathway is adapted so that components of a larger molecular weight move more slowly along the pathway than those of a lower molecular weight so that components of a lower molecular weight are delivered at the exit end of the capillary pathway first and components of a higher molecular weight are delivered later. The liquid may be moved through a capillary pathway by pressure or electrostatic forces, or both, and the adaptations that selectively control the movement of different size components along the pathway may involve the application of, for example, electric fields to a conductive capillary or the use of specialized polymers in the pathway. Fractions of the sample may then be assayed by known methods including, for example, laser induced fluorescence (LIF) and a variety of mass spectrographic processes.

Such devices normally provide useful results. However, the handling of the sample during such a process has been labor intensive and expensive. The sample is often collected on a resin that is held in a cartridge or capillary tray capable of withstanding high pressures. The cartridge is placed in a capillary pathway by means of high-pressure couplings, usually by hand. There is a need for a system capable of automatically moving samples into and out of a separation pathway.

The samples to be analyzed are often very small in volume and are mismatched with relatively large resin-containing cartridges that are commercially available. Resin-containing removable pipette tips for use with small volumes of materials are commercially available but have not been useful as components of high-pressure chromatography systems. There is a need for a system including relatively small sample-supply components.

Another problem of the prior art, especially in the analysis of low amounts of tryptic digests commonly used in proteomics analysis, is sample loss associated with nonspecific adsorption. Additionally, the use of nanoscale chromatography has practical limits on the volume of sample that can be loaded onto a resin column. It is an object of this invention to provide a sample-supply component that is useful in high-pressure liquid chromatography devices, that is suitable for use with small samples and that can be moved into and out of a capillary pathway easily and automatically.

It is another object of this invention to provide a sample-handling system suitable for automatic or robotic movement of small samples into and out of a capillary pathway.

SUMMARY

These and other objects are accomplished by the present invention, wherein a robotic system for handling components during chromatographic analysis includes a holder for positioning a sample within a separation pathway. The holder includes a first opening having an internally tapered shape and a second opening having an externally tapered shape. An interior of the holder, between the first and second openings, defines the separation pathway.

The robotic system further includes a hollow rigid member having an externally tapered shape, and a receiving portion having an internally tapered shape. The holder is positioned between the hollow rigid member and the receiving portion, wherein the externally tapered hollow rigid member engages the internally tapered first opening and the internally tapered receiving portion receives the externally tapered second opening to provide a sealed separation pathway extending from the hollow rigid member to the receiving portion.

In one aspect, the interior of the holder, between the first and second openings, includes a material that is adapted to support the sample material.

In another aspect, the robotic system includes robotic handling components for moving the holder into position between the receiving portion and the hollow rigid member. The robotic handling components also are adapted to apply axial pressure through at least one of the rigid member and the receiving portion to create a sealed separation pathway extending from the hollow rigid member to the receiving portion. The robotic handling components may be adapted to apply sufficient axial pressure such that the sealed separation pathway can withstand internal pressures of one thousand pounds per square inch.

In still another aspect, the hollow rigid member is an elongated needle having an externally tapered tip portion, wherein the robotic handling components apply axial pressure through the needle to create a sealed separation pathway extending from the needle to the receiving portion. The robotic handling components may be adapted to apply sufficient axial pressure through the needle such that the sealed separation pathway can withstand internal pressures of one thousand pounds per square inch.

In yet another aspect, the surface of the internally tapered receiving portion is a textured surface. The surface of the internally tapered receiving portion may include a plurality of ridges extending circumferentially around the internally tapered surface.

In still another aspect, the robotic system includes a recording and indexing sub-system for tracking and managing information regarding the analysis of the sample. The recording and indexing sub-system may be a computer.

DESCRIPTION OF THE DRAWINGS

The above, as well as other advantages of the present invention, will become readily apparent to those skilled in the art from the following detailed description of a preferred embodiment when considered in the light of the accompanying drawings.

DESCRIPTION OF THE EMBODIMENTS

Figure 1:
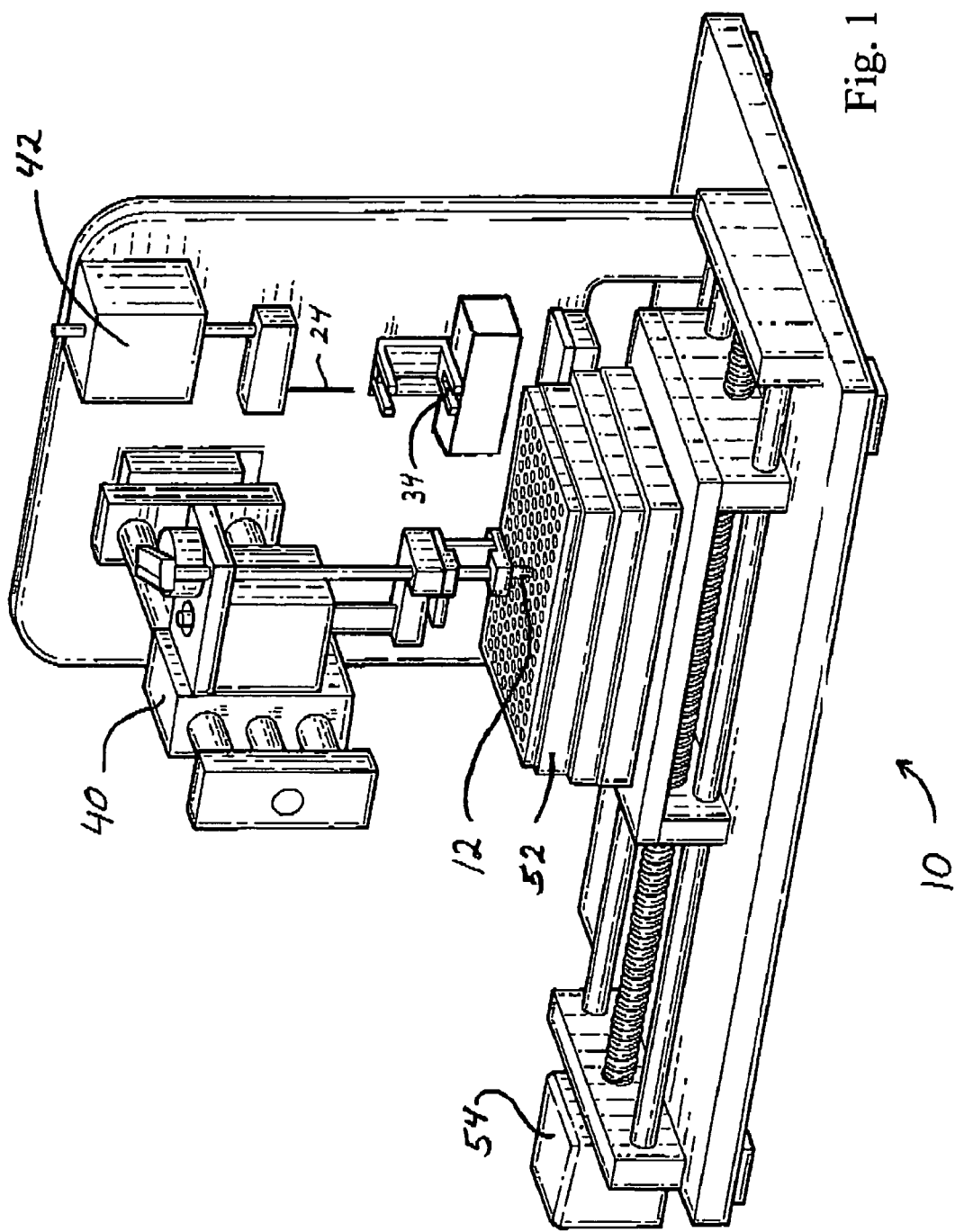
FIG. 1 is a perspective view of a robotic system of the present invention.
Figure 2:
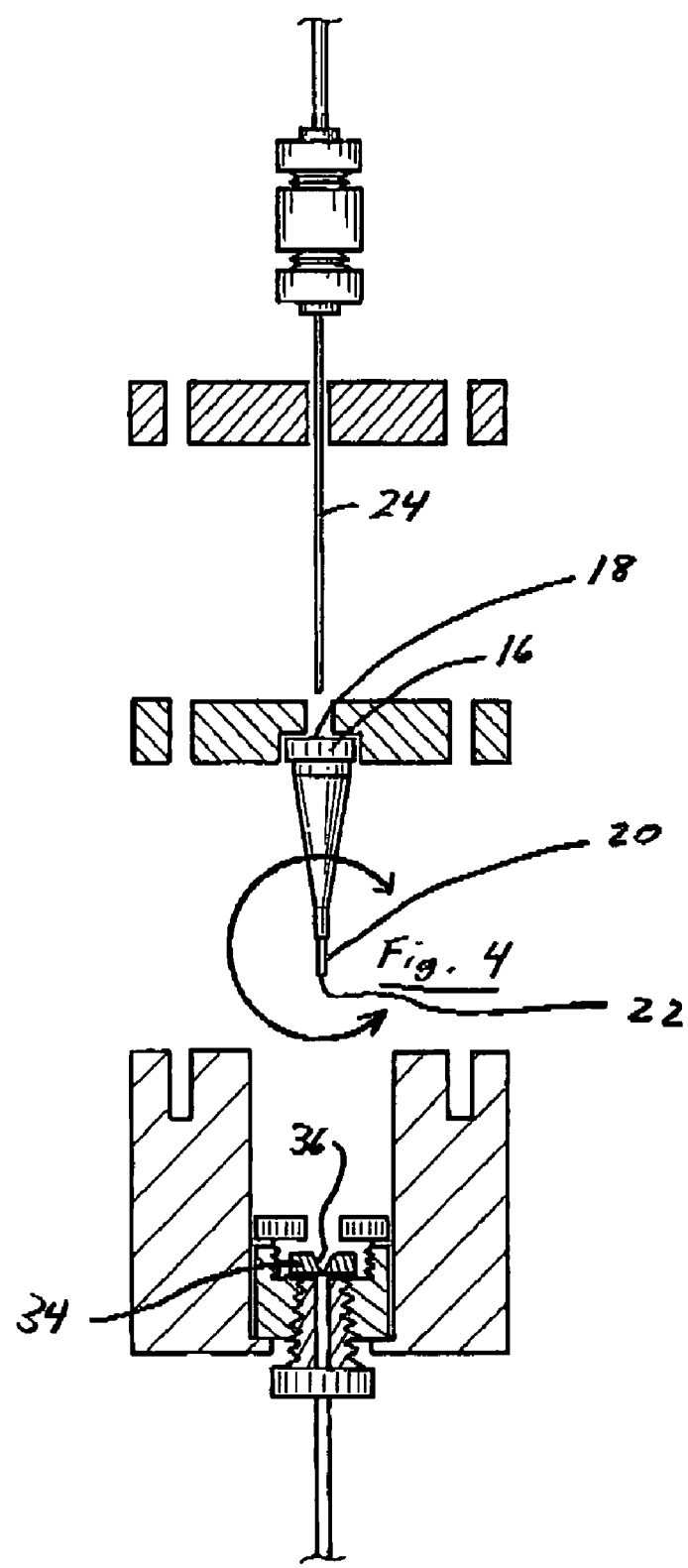
FIG. 2 is a plan view of the hollow rigid member, the holder, and the receiving portion of the robotic system shown in FIG. 1, prior to the components being brought into engagement with one another.
Figure 3:
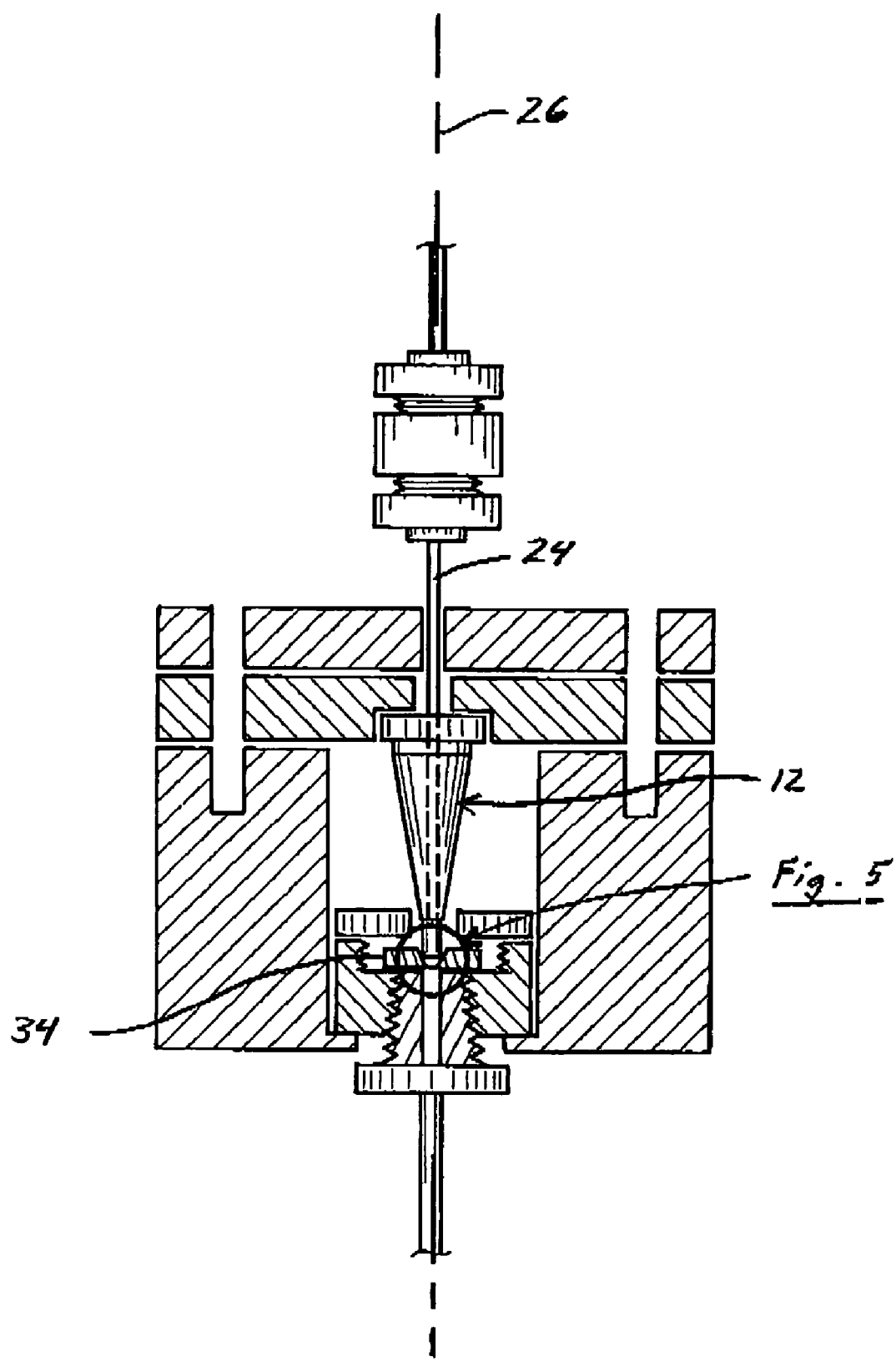
FIG. 3 is a plan of the hollow rigid member, the holder, and the receiving portion of the robotic system shown in FIGS. 1 and 2, after the components have been brought into engagement with one another.

The present invention relates to a robotic system 10 for handling components during chromatographic analysis of a sample. Referring to the Figures, the system 10 includes a holder 12 for positioning a sample within a separation pathway 14. The holder 12 is generally conical in shape. A first end 16 of the holder 12 defines a first opening 18 having an internally tapered shape. A second end 20 of the holder 12 defines a second opening 22 having an externally tapered shape. The separation pathway 14 is defined as the interior of the holder 12, between the first and second openings 18, 22.

A hollow rigid member 24 is mounted onto the robotic system 10. The hollow rigid member 24 is axially moveable along its' own axis 26. The hollow rigid member 24 includes a tip portion 28 having an externally tapered shape. As shown, the hollow rigid member 24 is an elongated needle having an externally tapered tip portion 28. Preferably, the angle 30 of the externally tapered tip portion 28 of the hollow rigid member 24 is closely aligned with the angle 32 of the internal tapered shape of the first end 16 of the holder 12.

A receiving portion 34 is mounted onto the robotic system 10. The receiving portion 34 includes a recess 36 having an internally tapered shape. Preferably, the angle 32 of the externally tapered second end of the holder is closely aligned with the angle 38 of the internal tapered shape of the recess 36 within the receiving portion 34.

The rigid hollow member 24, the holder 12, and the receiving portion 34 may be made from any suitable material. Preferably, the material that the holder 12 is formed from is relatively softer than the material selected for the receiving portion 34 and the hollow rigid member 24. This way, the engagement of the hollow rigid member 24 and the receiving portion 34 with the softer holder 12 will form a seal. For instance, good results have been obtained in prototypes having a hollow rigid member 24 made from stainless steel, a receiving portion 34 made from a hard plastic material such as an acetal resin, one of which is commercially available from DuPont under the trademark Delrin®, and a holder 12 made from a relatively softer plastic material. Although the holder 12 should be pliable in order to aid in forming a high pressure seal, the holder 12 must also be sufficiently rigid to effectively be handled and to withstand the internal pressures of the separation pathway 14.

The robotic system 10 includes robotic handling components 40 that move the holder 12 into position between the hollow rigid member 24 and the receiving portion 34. When properly aligned, the hollow rigid member 24, the holder 12, and the receiving portion 34 are all aligned co-axial with one another. Further, the robotic system 10 also includes robotic handling components 42 that move one or both of the hollow rigid member 24 and the receiving portion 34 axially closer to one another to capture the holder 12 therebetween. This movement brings the hollow rigid member 24 into contact with the internally tapered first opening 18 of the holder 12 and the second end 20 of the holder 12 into contact with the internally tapered recess 36 in the receiving portion 34.

The robotic system 10 can be designed wherein the hollow rigid member 24 moves downward and the receiving portion 34 simultaneously moves upward, or, alternatively, the receiving portion 34 can remain stationary, while the hollow rigid member 24 moves downward toward the receiving portion 34 after the holder 12 is positioned therebetween.

The robotic components 42 of the system 10 are designed to place sufficient axial pressure between the hollow rigid member 24 and the receiving portion 34 to create a sealed engagement between the tip 28 of the hollow rigid member 24 and the first opening 18 of the holder 12 and the second opening 22 of the holder 12 and the recess 36 of the receiving portion 34, thereby creating a sealed separation pathway 14 extending from the hollow rigid member 24 to the receiving portion 34. The robotic components 42 may be adapted to provide sufficient pressure to create a seal between the hollow rigid member 24, the holder 12, and the receiving portion 34 such that the separation pathway 14 can withstand internal pressures of one thousand pounds per square inch.

Preferably, an interior surface 44 of the holder 12 includes a support material 46 that is adapted to support the sample, such as a reverse phase resin to which a material for analysis, such as a protein fraction, is adhered. It has been found that a protein sample can be retained on this type of material substantially indefinitely without loss.

In operation a solvent or other capillary fluid will be moved under pressure along the separation pathway 14 to remove the sample from the support material 46 and to transport it through a downstream capillary column (not shown).

Figure 5:
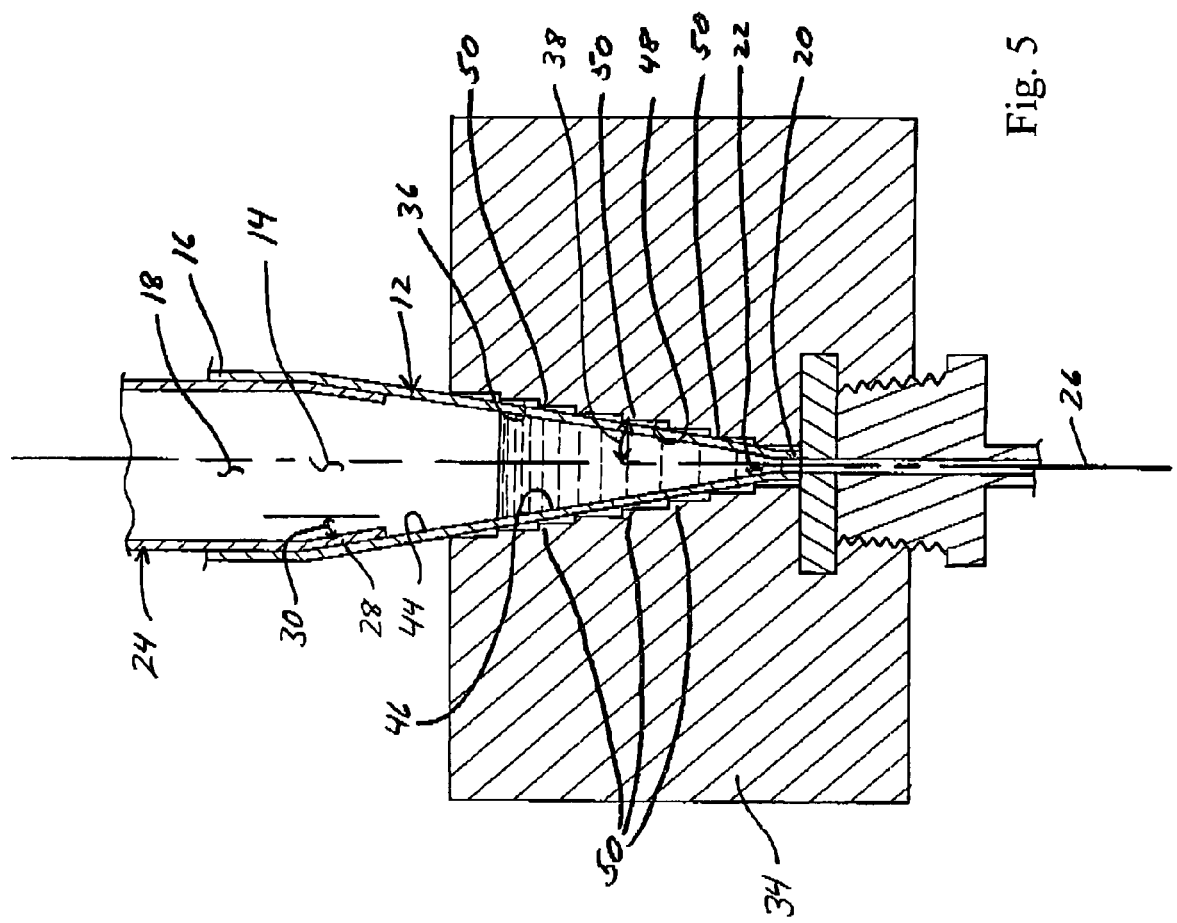
FIG. 5 is an enlarged sectional view of a portion of FIG. 3, as indicated by the encircled area of FIG. 3 labeled "FIG. 5".
Figure 4:
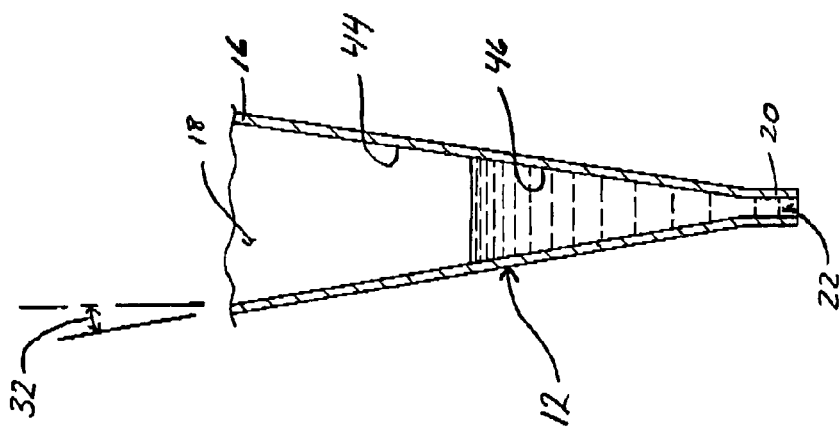
FIG. 4 is an enlarged sectional view of a portion of the holder, as indicated by the encircled area of FIG. 2 labeled "FIG. 4"

The internally tapered recess 36 within the receiving portion 34 may have a textured surface 48. Referring to FIG. 5, the surface 48 of the internally tapered receiving portion 34 includes a plurality of ridges 50 extending circumferentially therearound. The texture of the internally tapered surface 48 will allow a better seal formation between the externally tapered surface of the second end 20 of the holder 12 and the recess 36 formed within the receiving portion 34.

Ideally, a recording and indexing sub-system, such as a computer, is used for tracking and managing information regarding the analysis of the sample, and the controlling of the movements of the robotic components.

Referring again to FIG. 1, a delivery system 52 delivers a plurality of holders 12 to the robotic system 12. As shown, the delivery system 52 is a rack that holds a quantity of holders 12 that have samples pre-loaded therein for analysis. The robotic system 10 includes additional robotic components 54 that move the delivery system 52 to allow the holders 12 to be removed from the delivery system 52. The robotic handling components 40 of the system 10 retrieve the holders 12 from the rack and position them between the hollow rigid member 24 and the receiving portion 34 as described above.

In accordance with the provisions of the patent statutes, the present invention has been described in what is considered to represent its preferred embodiment. However, it should be noted that the invention can be practiced otherwise than as specifically illustrated and described.

What is claimed is:

1. A robotic system for handling components during chromatographic analysis of a sample comprising:

a holder for positioning a sample within a separation pathway, the holder including a first opening having an internally tapered shape and a second opening having an externally tapered shape, an interior surface of the holder between the first and second openings defining the separation pathway including a support material to support a sample;
a hollow rigid member having an externally tapered shape; and
a receiving portion having an internally tapered shape;
the holder positioned between the hollow rigid member and the receiving portion, wherein the externally tapered hollow rigid member engages the internally tapered first opening and the internally tapered receiving portion receives the externally tapered second opening to provide a sealed separation pathway extending from the hollow rigid member to the receiving portion.

2. The robotic system of claim 1 wherein the surface of the internally tapered receiving portion is a textured surface.

3. The robotic system of claim 1 wherein the surface of the internally tapered receiving portion includes a plurality of ridges extending circumferentially around the internally tapered surface.

4. The robotic system of claim 1 further including a delivery system for collecting samples onto the support material prior to assembly of the separation pathway.

5. The robotic system of claim 1 further including a recording and indexing sub-system for tracking and managing information regarding the analysis of the sample.

6. The robotic system of claim 5 wherein the recording and indexing sub-system is a computer.

7. The robotic system of claim 1 wherein the support material comprises a material to which a sample will adhere.

8. The robotic system of claim 7 wherein the support material comprises a reverse phase resin.

9. The robotic system of claim 1 further including robotic handling components for moving the holder into position between the receiving portion and the hollow rigid member and for applying axial pressure through at least one of the rigid member and the receiving portion to create a sealed separation pathway extending from the hollow rigid member to the receiving portion.

10. The robotic system of claim 9 wherein the robotic handling components are adapted to apply sufficient axial pressure through at least one of the rigid member and the receiving portion to create a sealed separation pathway extending from the hollow rigid member to the receiving portion that can withstand internal pressures of one thousand pounds per square inch.

11. The robotic system of claim 1, wherein the hollow rigid member is an elongated needle having an externally tapered tip portion.

12. The robotic system of claim 11 further including robotic handling components for moving the holder into position between the receiving portion and the hollow rigid member and for applying axial pressure through the needle to create a sealed separation pathway extending from the needle to the receiving portion.

13. The robotic system of claim 12 wherein the robotic handling components are adapted to apply sufficient axial pressure through the needle to create a sealed separation pathway extending from the hollow rigid member to the receiving portion that can withstand internal pressures of one thousand pounds per square inch.

14. A robotic system for handling components during analysis of samples comprising:
a hollow rigid member having a lower end;
a receiving portion having an internally tapered shape; and
a plurality of holders for selectively positioning samples between the hollow rigid member and the receiving portion, each holder having a tapered exterior surface suitable for engaging the internally tapered receiving portion, each holder including a first opening, a second opening, and a tapered interior surface between the first and second openings defining the separation pathway, the interior surface including a support material to support a sample, each holder being selectively positioned between the hollow rigid member and the receiving portion, at least one of the hollow rigid member and the receiving portion being movable toward the other so that the lower end of the hollow rigid member engages the holder first opening and the internally tapered receiving portion receives the externally tapered holder surface to provide a sealed separation pathway extending from the hollow rigid member to the receiving portion.

15. The robotic system of claim 8 wherein the support material in each of the plurality of holders comprises a reverse phase resin to which a sample will adhere.

16. The robotic system of claim 14, wherein the hollow rigid member is an elongated needle having an externally tapered tip portion.

17. The robotic system of claim 16 further including robotic handling components for selectively moving each holder into position between the receiving portion and the hollow rigid member and for applying axial pressure through the needle to create a sealed separation pathway extending from the needle to the receiving portion.

18. The robotic system of claim 17 further comprising a rack holding the plurality of holders the robotic handling components selectively moving each holder between the rack and the position between the receiving portion and the hollow rigid member.

19. A robotic system for handling components during analysis of samples, the system comprising:
a hollow rigid member having a lower end;
a receiving portion having an internally tapered shape; and
a plurality of externally tapered holders for selectively positioning samples between the hollow rigid member and the receiving portion, each holder having a first opening and a second opening, at least one of the hollow rigid member and the receiving portion being movable toward the other so that the lower end of the hollow rigid member engages the holder first opening and the internally tapered receiving portion receives the externally tapered holder surface to provide a sealed separation pathway extending from the hollow rigid member to the receiving portion, each holder having a tapered interior surface between the first and second openings defining the separation pathway, the interior surface including a support material to support a sample.

20. The robotic system of claim 19 wherein the support material in each of the plurality of holders comprises a reverse phase resin to which a sample will adhere.

* * * * *